(12) United States Patent
Marsh et al.

(10) Patent No.: US 11,007,324 B2
(45) Date of Patent: May 18, 2021

(54) DRUG DELIVERY DEVICE COMPRISING A PRISM

(71) Applicant: Sanofi, Paris (FR)

(72) Inventors: William Geoffrey Arthur Marsh, Buckinghamshire (GB); Anthony Paul Morris, West Midlands (GB); Mike Cameron Bainton, Kineton (GB); Matthew Meredith Jones, Warwick (GB)

(73) Assignee: Sanofi, Paris (FR)

( * ) Notice: Subject to any disclaimer, the term of this patent is extended or adjusted under 35 U.S.C. 154(b) by 371 days.

(21) Appl. No.: 15/533,302

(22) PCT Filed: Dec. 8, 2015

(86) PCT No.: PCT/EP2015/078922
§ 371 (c)(1),
(2) Date: Jun. 5, 2017

(87) PCT Pub. No.: WO2016/091850
PCT Pub. Date: Jun. 16, 2016

(65) Prior Publication Data
US 2017/0340833 A1    Nov. 30, 2017

(30) Foreign Application Priority Data

Dec. 8, 2014 (EP) .................................. 14306961

(51) Int. Cl.
*A61M 5/315* (2006.01)
*A61M 5/20* (2006.01)
(Continued)

(52) U.S. Cl.
CPC .......... *A61M 5/31553* (2013.01); *A61M 5/20* (2013.01); *A61M 5/2033* (2013.01);
(Continued)

(58) Field of Classification Search
CPC .............. A61M 2205/583; A61M 5/20; A61M 5/1454; A61M 2005/31518;
(Continued)

(56) References Cited

U.S. PATENT DOCUMENTS 5,261,882 A * 11/1993 Sealfon ............... A61M 5/1454
128/DIG. 12
5,647,854 A 7/1997 Olsen et al.
(Continued)

FOREIGN PATENT DOCUMENTS

EP        1250167       7/2005
JP     2002/191692      7/2002
(Continued)

OTHER PUBLICATIONS

International Preliminary Report on Patentability in International Application No. PCT/EP2015/078922, dated Jun. 13, 2017, 9 pages.
(Continued)

*Primary Examiner* — Lauren P Farrar
*Assistant Examiner* — Hamza A Darb
(74) *Attorney, Agent, or Firm* — Fish & Richardson P.C.

(57) ABSTRACT

The present disclosure relates to a drug delivery device comprising a dose setting member for setting user variable doses of a medicament and a display for indicating the dose set by the dose setting member. The display comprises a number wheel, which is rotationally coupled to the dose setting member and is provided with a series of markings on its outer circumference, and at least one prism deviating the image of the markings of the number wheel, e.g. by 90°.

17 Claims, 9 Drawing Sheets

(51) Int. Cl.
*A61M 5/31* (2006.01)
*A61M 5/32* (2006.01)
*A61M 5/145* (2006.01)

(52) U.S. Cl.
CPC .... *A61M 5/31526* (2013.01); *A61M 5/31541* (2013.01); *A61M 5/31563* (2013.01); *A61M 5/1454* (2013.01); *A61M 5/3286* (2013.01); *A61M 2005/3126* (2013.01); *A61M 2005/31518* (2013.01); *A61M 2205/581* (2013.01); *A61M 2205/583* (2013.01); *A61M 2205/585* (2013.01)

(58) Field of Classification Search
CPC .... A61M 2005/3126; A61M 2205/581; A61M 2205/585; A61M 5/31526; A61M 5/31541; A61M 5/2033; A61M 5/3286
See application file for complete search history.

(56) References Cited

U.S. PATENT DOCUMENTS

| | | | | |
|---|---|---|---|---|
| 2004/0054326 A1* | 3/2004 | Hommann | ........ | A61M 5/31553 604/131 |
| 2004/0064101 A1 | 4/2004 | Kowan et al. | | |
| 2004/0064104 A1* | 4/2004 | Miller | ........ | A61M 5/31525 604/207 |
| 2008/0033369 A1* | 2/2008 | Kohlbrenner | ....... | A61M 5/3155 604/207 |
| 2011/0276006 A1* | 11/2011 | Matthias | ........... | A61M 5/31525 604/189 |
| 2012/0211566 A1* | 8/2012 | Hensel | ............... | G06K 7/10732 235/462.42 |
| 2013/0211336 A1* | 8/2013 | Holmqvist | ........ | A61M 5/31558 604/189 |
| 2014/0046268 A1* | 2/2014 | Quinn | ............... | A61M 5/31541 604/209 |
| 2014/0378801 A1 | 12/2014 | Poulsen | | |

FOREIGN PATENT DOCUMENTS

| | | |
|---|---|---|
| WO | WO 2004/078241 | 9/2004 |
| WO | WO 2010/003569 | 1/2010 |

OTHER PUBLICATIONS

International Search Report and Written Opinion in International Application No. PCT/EP2015/078922, dated Apr. 25, 2016, 14 pages.

* cited by examiner 152  150

70  110
152  111

150
153
100
101

101
102
154
100
150

70
10
100
150
152

DRUG DELIVERY DEVICE COMPRISING A PRISM

CROSS-REFERENCE TO RELATED APPLICATIONS

This application is a U.S. national stage application under 35 USC § 371 of International Application No. PCT/EP2015/078922, filed on Dec. 8, 2015, which claims priority to European Patent Application No. 14306961.5, filed on Dec. 8, 2014, the entire contents of which are incorporated herein by reference.

TECHNICAL FIELD

The present disclosure is generally directed to a handheld injection device, i.e. a drug delivery device for selecting and dispensing a number of user variable doses of a medicament.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable drug delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Further types of energy storage may comprise compressed fluids or electrically driven devices with a battery or the like. Although many aspects of the present disclosure are applicable for all of these types of devices, i.e. for devices with or without a drive spring or the like energy storage, the preferred embodiments require some kind of energy storage.

These types of delivery devices generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the device that is used to set (select) a dose. During an injection, a plunger or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

The dosing section of drug delivery devices for selecting and dispensing a number of user variable doses of a medicament often comprises a display for indicating the selected dose to a user. This is especially important where a user may select a different dose each time depending on the state of health. There are mechanical displays, e.g. a drum with printed numbers on its outer surface, wherein the number corresponding to the actually selected dose is visible through a window or opening in the device. Although such mechanical displays are simple and reliable, they usually require a relatively large construction space which makes the devices bulky. In addition, the size of the numbers is in some cases too small for visually impaired users. Further, electronic displays are known, e.g. LCD displays, which have the benefit of a relatively large number size without requiring too much construction space. However, a downside of electronic displays is that they require an energy source and that such electronic components may be too expensive, especially in a disposable drug delivery device.

A disposable drug delivery device is known from WO 2004/078241 A1, wherein the display comprises a number sleeve with numbers printed on its outer surface. The device further comprises a housing, a cartridge holder for retaining a cartridge containing a medicament, a piston rod displaceable relative to the cartridge holder, a driver coupled to the piston rod, a dose setting knob coupled to the driver and fixed to the number sleeve, and an injection button. The number sleeve is in threaded engagement with the housing, such that the number sleeve rotates along a helical path in a first direction during dose selecting and rotates back into the housing in a second, opposite direction during dose dispensing.

An alternative design of the display is known for example from EP 1 250 167 B1, which shows a drug delivery device with a display similar to an egg-timer. A dose setting element is provided rotatable about an axis which is perpendicular to the longitudinal axis of the cartridge. The number display is arranged as a ring having respective markings with a pointer tip on the dose setting element pointing at the set dose marking. A downside of this display is that only every five number is indicated as a figure with dashes for every single unit. This makes it difficult to read the exact dose. Further, it may be difficult to identify the exact position of the pointer tip, which again raises the risk of misreadings.

SUMMARY

The present disclosure provides an improved drug delivery device which has a display for conveniently indicating the selected dose even for visually impaired users. Preferably, the display allows easy handling of the device and is reasonable regarding costs even for disposable devices. It is a further object to provide a simple and yet reliable display for e.g. use in a drug delivery device.

The drug delivery device comprises a dose setting member for setting user variable doses of a medicament and a display for indicating the dose set by the dose setting member. Typically, the number wheel is rotationally coupled to the dose setting member such that rotational dose setting movement of the dose setting member is transferred to the number wheel. This results in the actual set dose being displayed. The present disclosure is based on the idea to provide a series of markings on the outer circumference of a number wheel of the display and to deviate the image of the markings of the number wheel, preferably by 90°, by means of a prism. The outer circumference of a wheel is an area having enough space to arrange the series of markings with every single figure illustrated, or with every second figure illustrated and a line to mark intermediate positions. On the other hand, as the outer circumference of a wheel might not be the most convenient position of the markings to be readable by a user during dose setting and during dispensing, deviation is provided to increase ease of use.

Regarding the direction of the deviation, it is convenient for some users if the display faces in the direction in which actuation is required during dose setting and/or dose dispensing. For example, if rotation in a plane is required for dose setting and pushing perpendicular to said plane is required for dose dispensing the display may be arranged next to this plane. Preferably, the number wheel is rotatable about an axis, wherein the prism is arranged such that the image of the markings of the number wheel is deviated in a direction parallel to said axis.

According to a preferred embodiment, the at least one prism is a triangular prism, and the series of markings is provided reversed (mirrored) on the outer circumference of the number wheel to be readable through the prism.

As an alternative, a penta-prism may be used instead of a simple (triangular) prism allowing the transmission of an image through a right angle without inverting it, that is, without changing the image's handedness. Thus, the series of markings is provided non-mirrored on the outer circumference of the number wheel.

Preferably, the surface of the prism is designed to provide a magnification of the markings on the number wheel. This allows it even with limited space available on the outer circumferential surface of the number wheel to provide an individual figure for every unit (or every second unit) of dose to be set which still is conveniently readable by a user.

An ergonomic design of the drug delivery device may comprise a housing having a longitudinal axis defined by a compartment for receiving a cartridge, wherein the dose setting member is arranged rotatable within the housing with its axis of rotation being perpendicular to the longitudinal axis of the housing.

In a preferred embodiment, the drug delivery device further comprises a power reservoir applying an axial load on a plunger which acts on the cartridge bung. To avoid uncontrolled dispensing from the cartridge, a retaining member is provided which is coupled to the plunger to hold the plunger against the force of the power reservoir. A release member which is coupled to the retaining member allows movement of the retaining member and, thus, the plunger for a desired distance corresponding to the dose to be dispensed. In other words, a tensile load acts on the retaining member under the action of the power reservoir and the retaining member is released during dose dispensing. An example of a power reservoir suitable for the present disclosure is a compression spring.

Preferably, the drive mechanism of the drug delivery device comprises the housing, the plunger, the power reservoir, the retaining member and the release member. The plunger which is coupled to the retaining member is suitable for acting on a bung of the cartridge if retained in the housing. The power reservoir, preferably a pre-strained pressure spring, is arranged between the housing and the plunger, for example coaxially with the longitudinal axis defined by the cartridge or its compartment. The release member is preferably operable between a first state and a second state. In its first state the release member constrains the retaining member to the housing, thus preventing movement of the plunger under the action of the power reservoir. In its second state the release member is movable relative to the housing, thus allowing movement of the plunger) by means of the power reservoir.

The use of a spring or the like has the benefit of reducing the user force required to expel the contents of the cartridge. A pre-strained spring has the further advantage to reduce the force required during dose setting. As an alternative to a pre-strained spring, a spring or other suitable power reservoir may be used, which is charged or strained during dose setting. Another benefit of devices where the force required to expel the contents of the cartridge is provided by a power reservoir instead of the user is that a dial extension of the device may be avoided, which means that the size of the device remains the same irrespective of whether a dose is set or the amount of the set dose. This makes the device more compact and user-friendly.

The retaining member is preferably a flexible element with high tensile modulus and strength, like glass or aramid fibre reinforced poly-urethane. The retaining member may have the form of a belt or cable. As the load acting on the retaining member is a tensile force, the drive mechanism may be further reduced in size by winding the retaining member on a spool or the like which is not possible with pressure loaded piston rods. In addition, the retaining member may be compact in size compared to a piston rod which requires a compressive stiffness for transmitting axial pressure loads.

The plunger may be constrained to one end of the retaining member. Preferably, it is axially, i.e. in the longitudinal direction of cartridge, fixed to the retaining member. As an alternative, the plunger may be a unitary part of the retaining member, for example a widened end thereof.

According to a preferred embodiment, the release member is in its second state rotatable relative to the housing. For example, the retaining member is attached to and wound on a drum or spool which is in gear engagement with the release member. Thus, rotation of the release member allows the retaining member to unwind from the drum or spool a desired distance corresponding to the distance the plunger is pushed into the cartridge under the action of the spring or the like. As an alternative, the retaining member may be directly attached to and wound on the release member.

The dose setting member may be rotatable relative to the release member during dose setting and may rotate together with the release member during dose dispensing. Preferably, the dose setting member and the release member are arranged rotatably within the housing with their respective axis of rotation being perpendicular to the longitudinal axis of the housing. This arrangement of the component parts has advantages regarding size and ease of use of the device. The dose setting member and the release member may be arranged coaxially. This common axis may however be offset from the axis of a drum or spool to which the retaining member may be attached.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring force needed for dispensing very high doses, while still being suitable for a wide range of patients needing different dose sizes. Preferably, the limits for the minimum dose and the maximum dose are provided by hard stop features. For example, the rotation of the dose setting member relative to the housing is limited by rotational stops defining a minimum dose position and a maximum dose position. The minimum dose stop has to be robust enough to withstand the load exerted by the power reservoir via the retaining member.

The drug delivery device may further comprise a trigger which is axially movable in the direction of the axis of rotation of the dose setting member. Actuation of the trigger switches the release member between its first and second state. For example, the trigger may act on a clutch which constrains the release member to the housing in its first state, i.e. when the trigger is not actuated, and which allows rotation of the release member for dose dispensing as soon as the trigger is actuated.

A dial gear may be provided in the drug delivery device which is rotationally coupled to the release member during dose dispensing. Thus, decelerating the dial gear may be used to control dispensing speed. In general, there are different ways to create the friction decelerating a dial gear or the like component of the device. For example a component part may be pressed against for the dial gear. As an alternative, a ratchet may be provided which may be brought into and out of engagement with the dial gear. Further, a flexible element may be used which acts on the dial gear. According to a preferred embodiment the friction means comprises a multi-plate clutch system acting between a stationary component part and the (rotating) dial gear. The multiplate clutch system may comprise a spring, at least one first clutch plate, which is rotationally constrained to the dial gear, and at least one second clutch plate, which is rotationally constrained to the housing at least during dose dispensing. The spring may press the clutch plates against each other, thus creating friction between a rotating and a non-rotting plate, which thus decelerates the dial gear.

Preferably, the multi-plate clutch system further comprises a cage which is rotationally constrained to the housing at least during dose dispensing and which is rotationally constrained to the second clutch plate(s), wherein the spring biases the cage towards at least one component part of the dial gear. Amending the axial position of the spring, the cage and/or the dial gear results in a variation of the friction decelerating the dial gear during dose dispensing.

According to a further embodiment of the present disclosure a dispensing speed control mechanism is provided for use in an injection device having a release button or trigger, which is displaceable to initiate dispensing of a set dose, a first component part, which is driven by a power reservoir during dose dispensing, and a second component part, which is stationary during dose dispensing. The speed control mechanism comprises friction means for decelerating the first component part during dose dispensing depending on the position of the release button. In other words, the user is able to control the dispensing speed by increasing or decreasing friction within the device and thus use either the full dispensing speed provided by the power reservoir or a speed reduced due to the internal friction.

Preferably, the release button or trigger has to be depressed a first distance to initiate dose dispensing, e.g. by releasing a clutch, and may then be depressed further a second distance to control and amend dispensing speed. This may include examples where due to the position of the release button there is either friction decelerating the driver or not. As an alternative, the magnitude of the friction decelerating the driver may be individually and preferably steplessly amended or adjusted by varying the position of the release button or trigger.

In a preferred embodiment, the friction is at a high level just after the button or trigger is depressed the first distance and decreases as the button or trigger is pressed further for the full amount or fractions of the second distance. Typically, the release button or trigger is pressed in an axial direction of the housing and relative to the housing.

According to a further embodiment of the present disclosure the handheld injection device comprises clicker components. Different clicker mechanisms may be active during dose setting and dose dispensing. For example, a dose setting feedback may be generated between the housing and a dial member. A dose dispensing feedback may be generated between a chassis fixed to the housing and the release member. To provide an additional non-visual, i.e. an audible and/or tactile, feedback to a user only at the end of dispensing of a set dose, a clicker between the chassis and the dial gear may be active as the device returns to its minimum dose stop. To differentiate between these feedback signals, the end of dose dispensing feedback, which is generated only at the end of dispensing of a set dose, is distinct from the further feedback(s). For example, a different sound may be generated.

In addition to the non-visual feedbacks, drug delivery devices usually have a display indicating the actually set dose. For example, a number wheel may be arranged coaxially with and rotationally coupled to the dose setting member with a series of markings being provided on the outer circumference of the number wheel.

The drug delivery device may comprise a dose dial grip for dose setting and clutch means (which may comprise one or more clutches) coupling the dose dial grip rotationally to the dose setting member during dose setting and rotationally de-coupling the dose dial grip from the dose setting member and coupling the dose setting member rotationally to the release member during dose dispensing. Preferably, this clutch is actuated by the trigger. This arrangement of the clutch has the benefit that the dose dial grip is free to spin during dose dispensing without interfering with the components moving during dispensing. As an alternative, the dose dial grip may be constrained to the housing during dispensing.

According to a further aspect of the present disclosure, the drive mechanism further comprises a nut which is guided axially displaceable and non rotatable with respect to one of the dose setting member and the release member. For example, the nut and the dose setting member or the release member are provided with corresponding splines and notches. The nut further has a thread engaging a thread of the other of the dose setting member and the release member such that relative rotation between the dose setting member and the release member during dose setting causes the nut to move towards an end stop. According to the present disclosure an injection device may comprise a cartridge containing a medicament and a drive mechanism as mentioned above. The nut and the end stop may be provided in the drive mechanism of the injection device such that the nut prevents setting of a dose exceeding the (dispensable) amount of a medicament in the injection device. In other words, the end stop preferably defines the length of a track on which the nut travels during dose setting, wherein the length of the track corresponds to the total (dispensable) amount of medicament in the cartridge.

The device according to the present disclosure is preferably a disposable injection device. It has low torque requirements to set a dose, low force requirements to trigger dispense of medicament and permits any dose to be selected within a range of zero to a pre-defined maximum. It has relatively low part count, very compact size and is particularly attractive for cost sensitive device applications.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-GlyGlu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(0)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)(Lys)6-NH2, H-Asn-(Glu)5-des Pro36, Pro37, Pro38 [Met(O)14, Trp (O2)25, Asp28] Exendin-4(1-39)-(Lys)6-NH2, or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and c have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and c have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

The present disclosure will now be described in further detail with reference to the accompanying schematic drawings, wherein.

DETAILED DESCRIPTION

Figure 1:
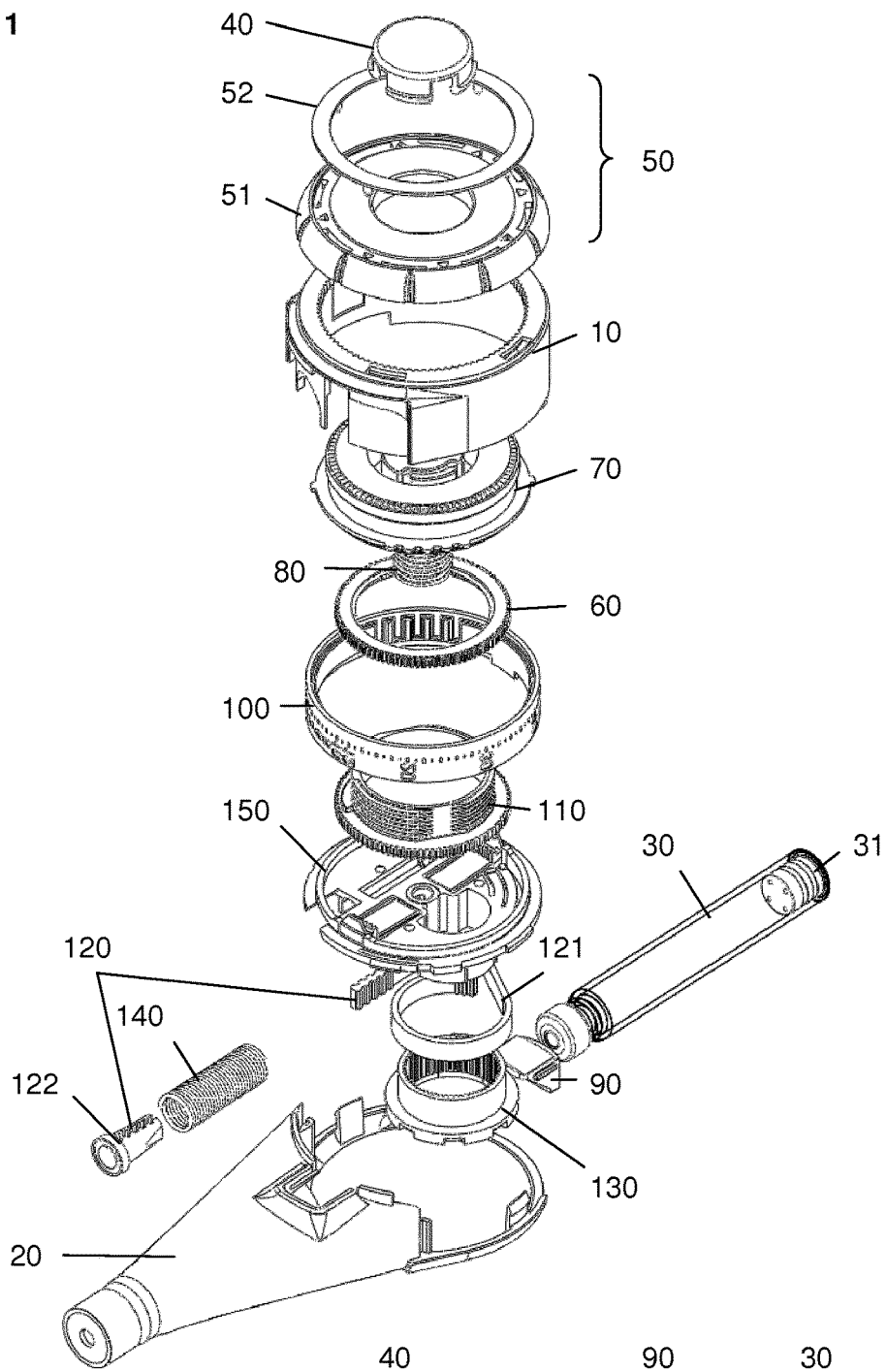
FIG. 1 shows an exploded view of an injection device comprising a drive mechanism.
Figure 2:
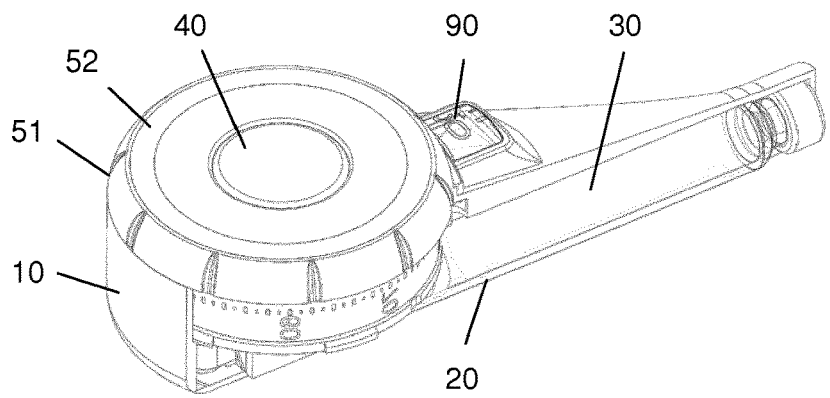
FIG. 2 shows a perspective view of the device of FIG. 1.

FIGS. 1 and 2 show views of the drug delivery device. FIG. 1 illustrates the component parts incorporated into the injection device which are a body 10, a cartridge holder 20, a trigger 40, a dial member 50 comprising a dial 51 and a dial cover 52 a medicament cartridge 30, a last dose nut 60, a dial gear 70, a trigger spring 80, a prism 90, a number wheel 100, a release gear 110, a belt assembly 120, a belt gear 130, a main spring 140 and a chassis 150.

The body 10 and the cartridge holder 20 form a housing which has a distal end at the side receiving the cartridge 30 (right hand side in FIG. 2) and an opposite proximal end. The cartridge holder defines a longitudinal axis of the housing. A rotational axis is provided perpendicular to this longitudinal axis with the trigger 40, the dial member 50, the last dose nut 60, the dial gear 70, the trigger spring 80, the number wheel 100 and the release gear 110 are arranged concentrically about this rotational axis.

The medicament cartridge 30 is housed within the cartridge holder 20. The cartridge holder 20 is rigidly constrained in the body 10. The cartridge holder 20 provides location and containment of the medicament cartridge and prism 90.

Figure 3:
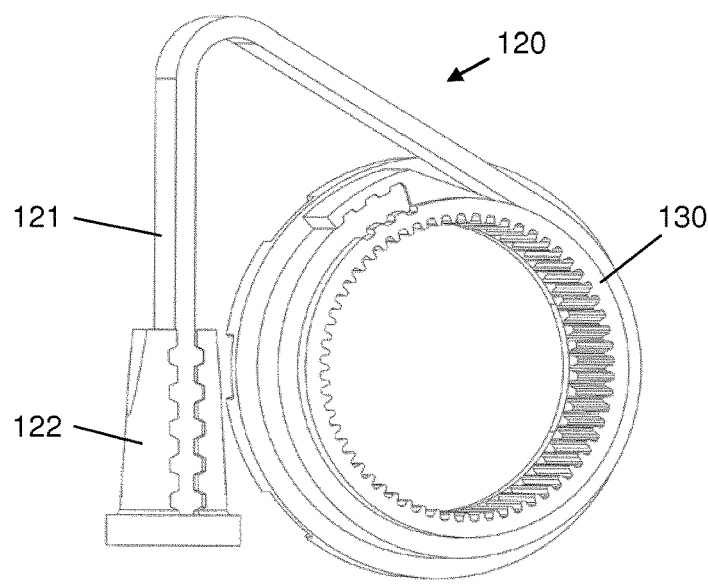
FIG. 3 shows a top view of components of the drive mechanism of FIG. 1.

The belt assembly 120 comprises a belt 121 and a plunger 122. The belt 121 is a flexible element with high tensile modulus and strength. Suitable materials include glass or aramid fibre reinforced poly-urethane. Features at each end of the belt 121 provide axial constraint and allow it to carry a tensile load. The distal end of the belt 121 is connected to the plunger 122 via spline features as shown in FIG. 3. The opposite end of the belt 121 is restrained by the belt gear 130 and partially wound onto it. FIG. 3 shows the belt 121 assembled to the belt gear 130 in the "as delivered" condition (prior to any doses being delivered).

Figure 4:
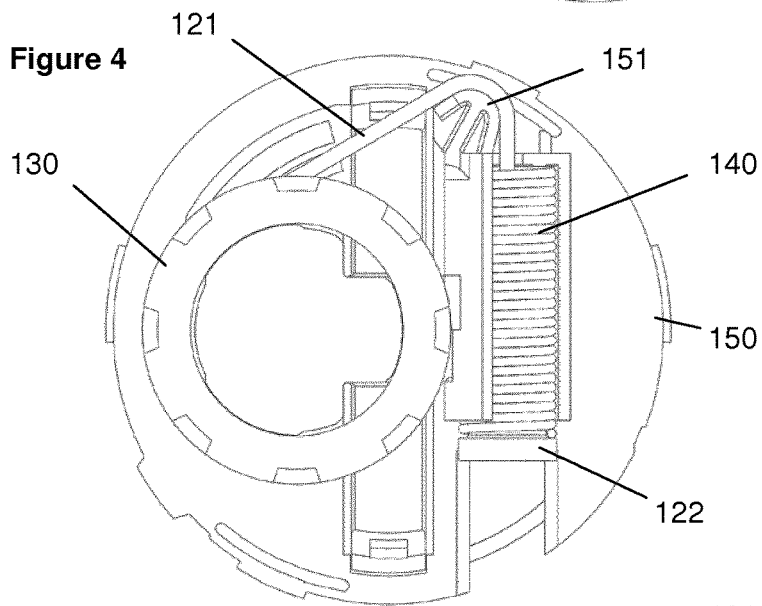
FIG. 4 shows a bottom view of components of the drive mechanism of FIG. 1.

The distal face of the plunger 122 abuts a bung of the medicament cartridge 30 and the main spring 140 acts directly on the proximal surface of the plunger 122. It is the main spring 140 acting on the plunger 122 that drives the bung axially in order to deliver medicament. Tension in the belt 121 prevents the main spring 140 releasing and, therefore, by controlling the release of the belt 121, accurate control of the medicament delivery can be achieved. FIG. 4 shows the main spring 140 in its fully compressed state, i.e. the state prior to dispensing the first dose, interposed between the plunger 122 and a bearing face of the chassis 150. The belt 121 is held in tension by the main spring 140 and follows a curved path in the device defined by a belt guide feature 151 on the chassis 150.

The main spring 140 is supplied to the user in the fully charged state (near "coil bound"). It acts between the proximal face of the plunger 122 and an abutment on the chassis 150. Tension in the belt 121 prevents the energy stored in the main spring 140 from being released until a dose is dispensed.

Figure 5:
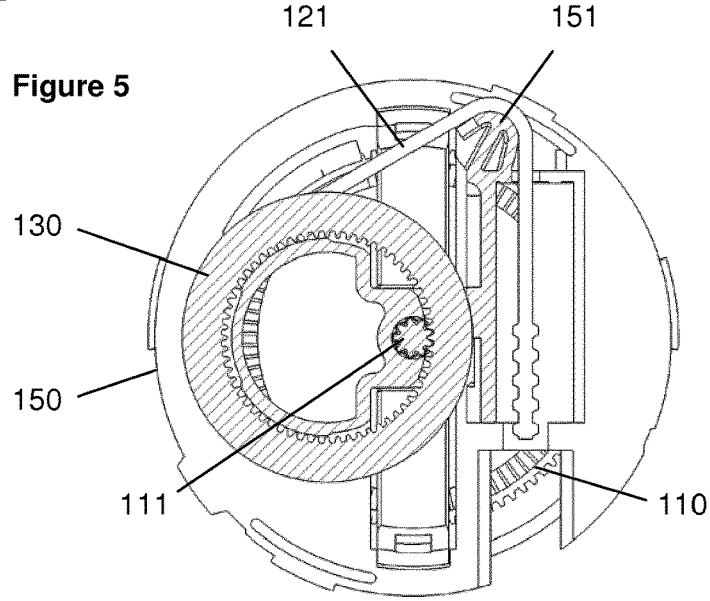
FIG. 5 shows a perspective view of components of the drive mechanism of FIG. 1, FIGS. 6a, 6b show sectional views of components of the device of FIG. 1, FIGS. 7a, 7b show details of the device of FIG. 1 in the minimum dose position and in the maximum dose position.

The belt gear 130 controls release of the belt 121 through a geared interface with a pinion 111 of the release gear 110. It is radially constrained by the chassis 150 via a combination of abutments. The combined effect of these abutments ensure that the resultant force acting on the belt gear 130 from the belt 121 biases the geared interface with pinion 111 of the release gear 110 into engagement as shown in FIG. 5. This acts to minimize backlash between the gears and also reduce the risk of disengagement in the event of shock loading.

Figure 6A:
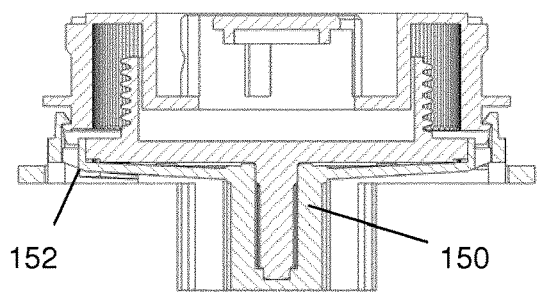
Figure 6B:
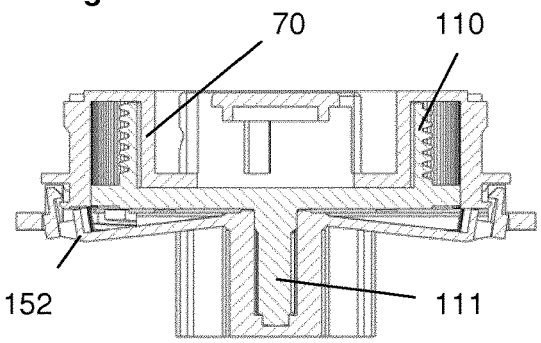

The chassis 150 locates the mechanism within the body 10 and is rigidly fixed into the body 10 via spline and spring clip features. It provides location for the belt gear 130 and belt 121. Flexible features within the chassis 150 (chassis locking arms 152) fix the release gear 110 rotationally during dialing (FIG. 6a) but disengage to allow rotation during triggering (FIG. 6b). Abutments adjacent to these chassis locking arms 152 provide tangential support and prevent excessive deflection when loaded by the release gear 110.

Figure 7A:
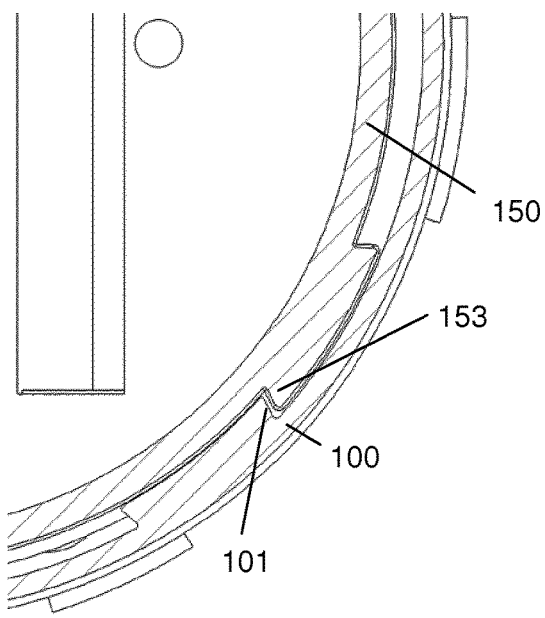
Figure 7B:
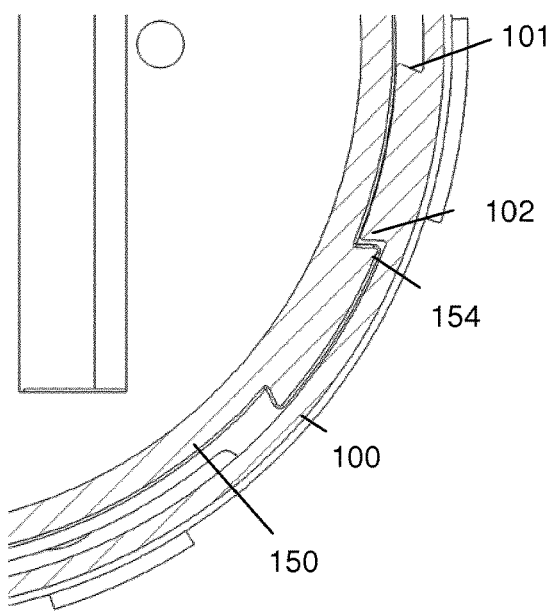
Figure 8:
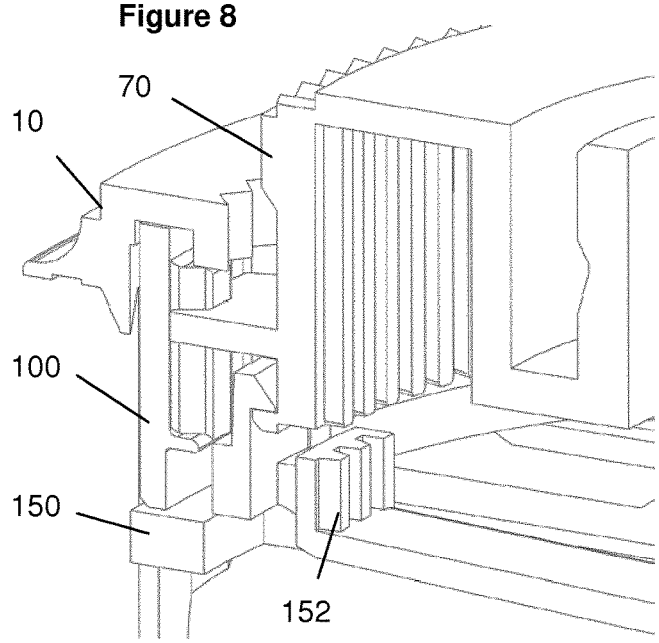
FIG. 8 shows a detail of the device of FIG. 1.

The number wheel 100 incorporates stop features 101, 102 which engage with abutments 153, 154 on the chassis 150 and correspond with the minimum (FIG. 7a) and maximum (FIG. 7b) dose set. This restricts the maximum dose that may be set and creates the end of dose stop when the mechanism returns to the zero unit position. The number wheel 100 is printed with a series of numbers on the external surface which create the dose display when viewed through the prism 90. The number wheel 100 is rotationally coupled to the dial gear 70 as shown in FIG. 8. Further, the number wheel is axially located between the chassis 150 and the body 10 and radially constrained by the body 10.

Figure 10:
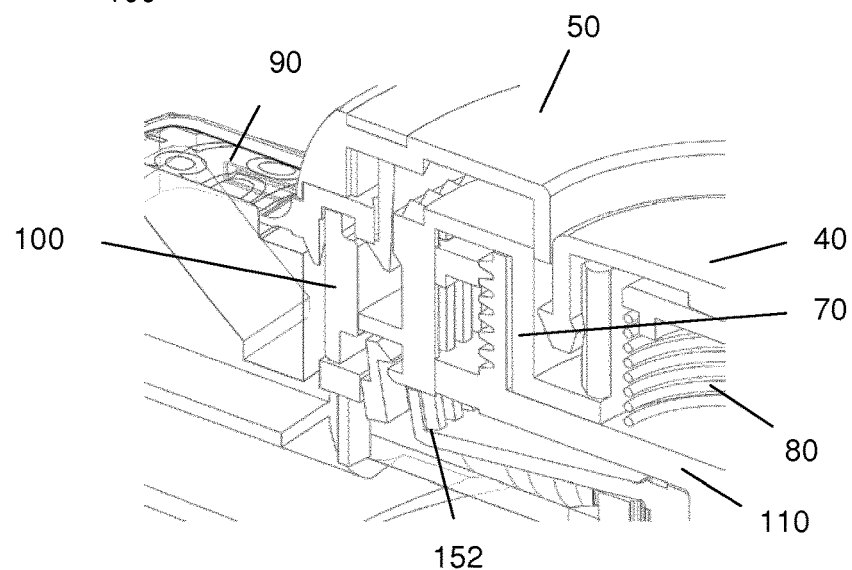
FIG. 10 shows a detail of the device of FIG. 1 in the dose dispensing condition.

The dose set is displayed on the outer surface of the device to provide feedback to the user. In this embodiment, the prism 90 reflects the display from the number wheel 100 so that the dose is displayed on the front face of the device (upper side in FIG. 2). The prism 90 is retained within the cartridge holder 20 and body 10 once assembled as shown in FIG. 10. The prism 90 uses the phenomenon of "Total Internal Reflection" to achieve reflection of the number without any special treatment to the surfaces (such as metal coating). The nature of this prism is that the display is mirrored. To account for this, the printing on the number wheel 100 is reversed so the net effect provides a conventional dose number display. An additional function of the prism 90 is that the surfaces can be designed to also provide magnification, in addition to the primary function of reflection.

Alternative prism arrangements (for example a pentaprism) could perform the same function without mirroring the display if required. An alternative embodiment negates the requirement for the prism 90 component and displays the dose on the side of the device. The number wheel 100 is then printed with conventional, non-mirrored, text and a small window is formed in the side of the body 10.

Figure 9:
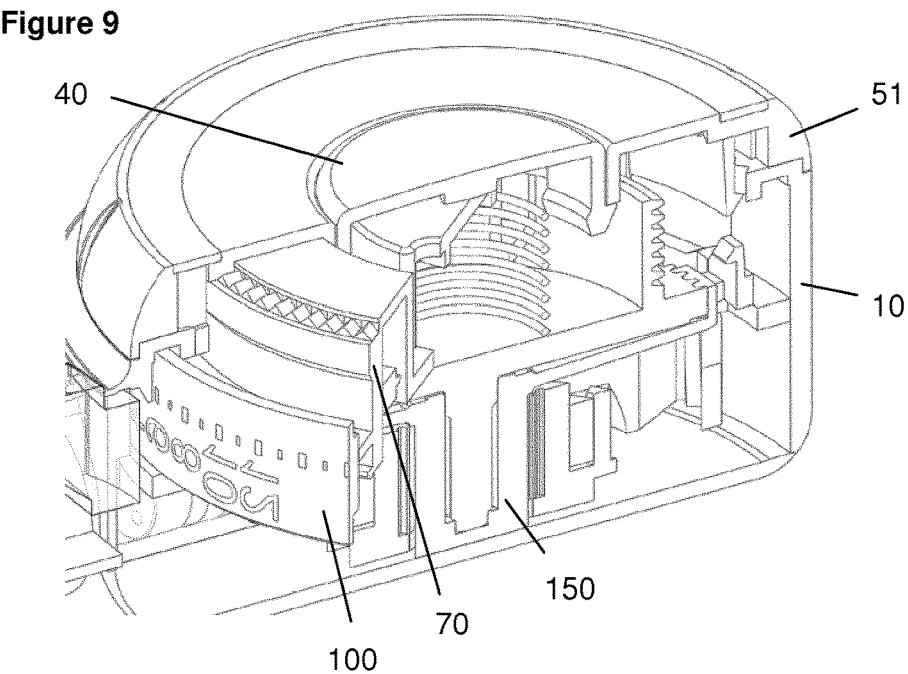
FIG. 9 shows a detail of the device of FIG. 1 in the dose setting condition.

The dial gear 70 is rotationally coupled to the dial member 50 during dialing (FIG. 9) and rotationally coupled to the release gear 110 during dispense (FIG. 10). The dial gear 70 may translate axially between abutments provided by the release gear 110 and the dial member 50 and is biased into contact with the dial member 50 via the trigger spring 80 when the trigger 40 is not depressed. The trigger spring 80 acts between the dial gear 70 and release gear 110. The chassis locking arms 152 are axially coupled to the dial gear 70 with snap clips which permit relative rotation.

Figure 11:
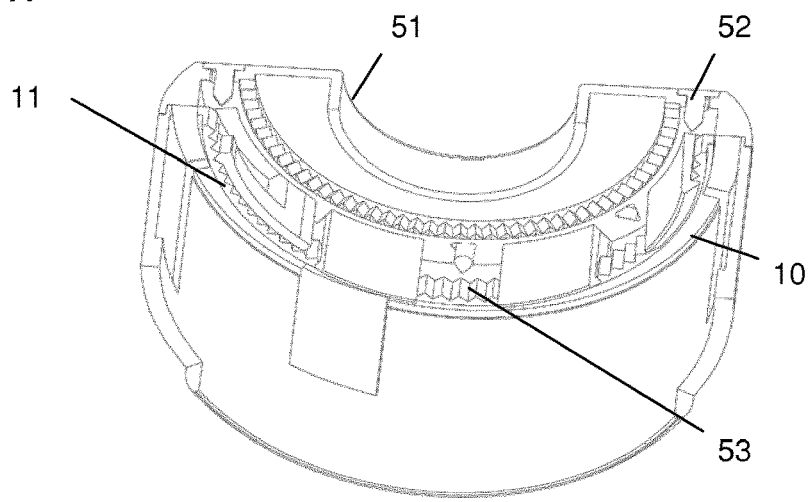
FIG. 11 shows a detail of the device of FIG. 1.

The dial member 50 comprises the dial 51 and the dial cover 52 which are permanently and rigidly fixed together. The dial member 50 is axially and radially located in the body 10 via snap clips and the rotational position is detented via a flexible cantilever arm 53 locating in radial ratchet teeth 11 within the body 10 (FIG. 11). These detent features provide positive feedback to the user during dialing and align the dial member 50 and number wheel 100 with the body 10 so the units of the dose display accurately align with the prism 90.

Figure 12:
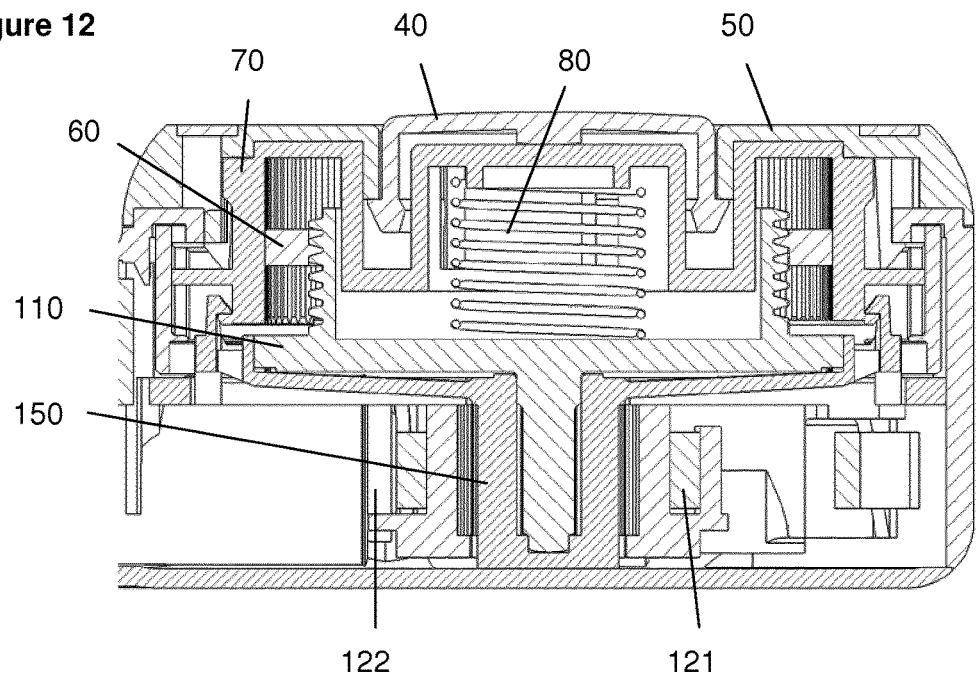
FIG. 12 shows a sectional view of a detail of the device of FIG. 1.

The trigger 40 is snap fitted into the dial member 50 and axially constrained between abutments on the dial member 50 and dial gear 70. The user may axially translate the trigger 40 between these abutments by overcoming the force of the trigger spring 80 which is transferred through the dial gear 70 (FIG. 12).

During dose setting, the release gear 110 is in toothed engagement with the belt gear 130 and rotationally fixed by the chassis locking arms 152. When the trigger 40 is depressed, the release gear 110 is rotationally coupled to the dial gear 70 and is released from the chassis locking arms 152. It is axially constrained between the dial gear 70 and chassis 150 and is biased toward the chassis 150 abutment by the trigger spring 80.

The mechanism incorporates a last dose nut 60 to prevent setting of a dose greater than that which remains within the medicament cartridge. This is positioned between the dial gear 70 and release gear 110 since the dial gear 70 rotates relative to the release gear 110 during dose set and not during dispense. The last dose nut 60 is splined to the inner surface of the dial gear 70 and threaded to the release gear 110 such that clockwise rotation of the dial member 50 rotates the last dose nut 60 and translates it towards the last dose stop on the release gear 110.

Figure 13:
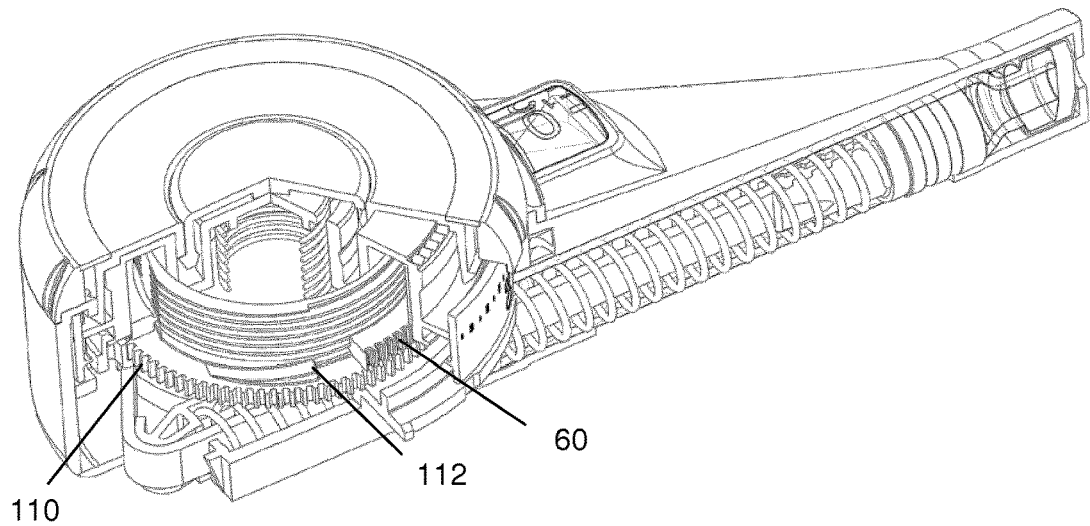
FIG. 13 shows the device of FIG. 1 with an empty cartridge.
Figure 14:
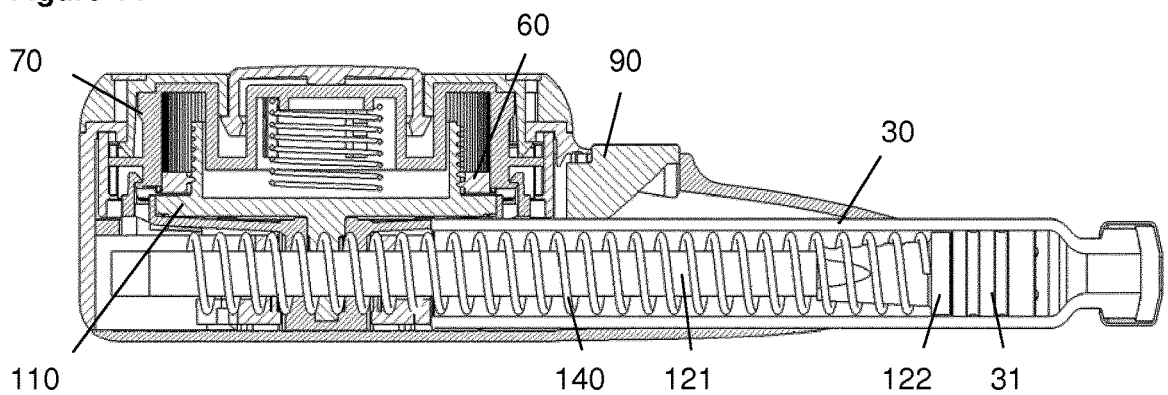
FIG. 14 shows the device of FIG. 1 with an empty cartridge.

The last dose nut 60 is successively translated towards the stop as doses are set until the cartridge dose limit is reached. At this point the last dose nut 60 contacts the abutment 112 on the release gear 110 which prevents further clockwise rotation of the last dose nut 60 and, therefore, rotation of the dial gear 70 and dial member 50. FIGS. 13 and 14 show the device shortly before the nut contacts abutment 112. The number of permissible rotations of the last dose nut 60 is determined by the capacity of the cartridge 30.

Figure 15:
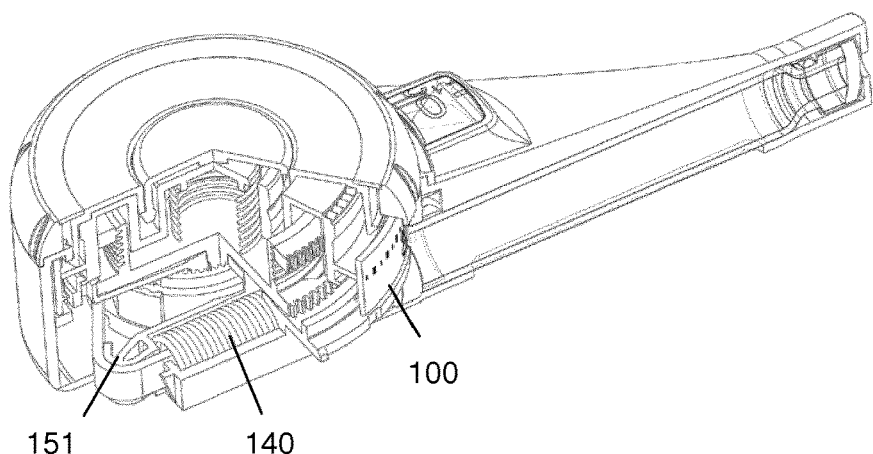
FIG. 15 shows the device of FIG. 1 with a full cartridge prior to dose setting.
Figure 16:
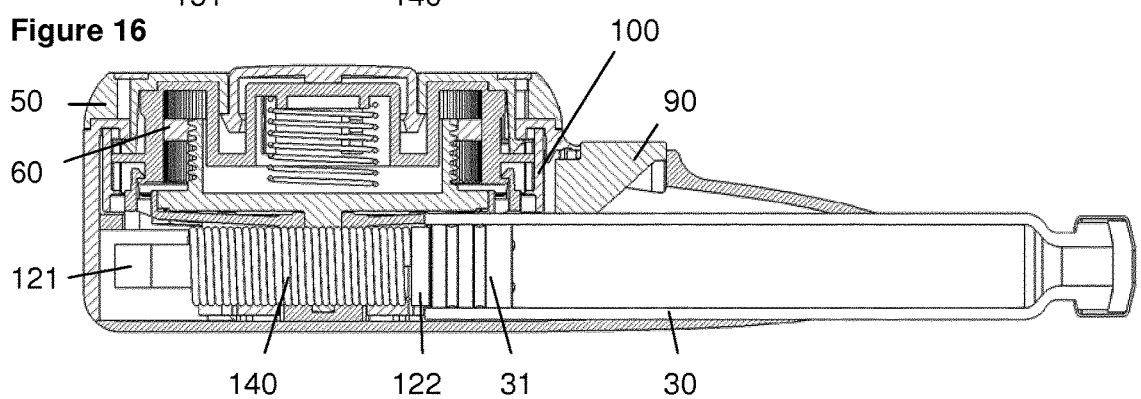
FIG. 16 shows the device of FIG. 1 with a full cartridge prior to dose setting.

The dial member 50 is rotated by the user in a clockwise direction to set a dose starting from the position shown in FIGS. 15 and 16. The dose can be cancelled by rotating the dial member 50 in a counter-clockwise direction either before any dispense or, alternatively, if the trigger 40 is released mid-dispense, the remaining dose may be cancelled.

Figure 17:
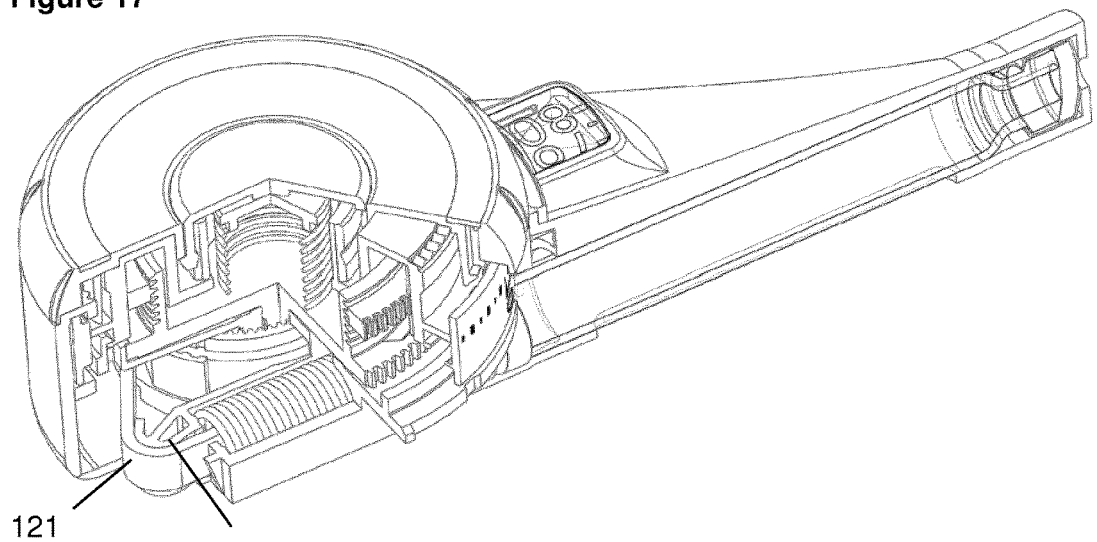
FIG. 17 shows the device of FIG. 1 with a full cartridge with maximum dose set.
Figure 18:
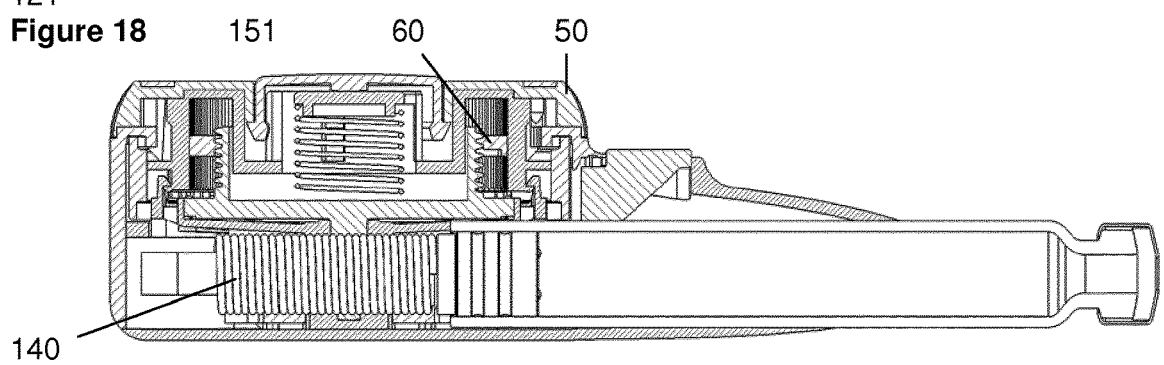
FIG. 18 shows the device of FIG. 1 with a full cartridge with maximum dose set.

The selected dose is displayed through the body 10 via the number wheel 100 and prism 90 as described previously. Irrespective of whether the dial member 50 is rotated clockwise or counter-clockwise the dose displayed will always indicate the dose to be dispensed. In addition, the dose display also decrements as the dose is dispensed and thus displays the dose remaining to be dispensed. As the dose is dialed up the number wheel 100 is driven away from the zero unit stop 153 on the chassis 150 and towards the maximum unit stop 154. The dial member 50 can be rotated by the user in both clockwise and counter-clockwise directions when the number wheel 100 is not in contact with the zero dose stop abutment 153 or maximum dose stop abutment 154 of the chassis 150. The zero unit abutment 153 prevents counter-clockwise rotation of the dial member 50 below the zero unit position. The maximum dose abutment 154 prevents setting of a dose greater than the mechanism maximum which is depicted in FIGS. 17 and 18.

The detent features 11, 53 between dial member 50 and body 10 controls the position of the dial member 50 to ensure that discrete units are selected and that the spline features between dial member 50 and release gear 110 are correctly aligned to permit spline meshing when the device is triggered.

During dose setting, the release gear 110 is biased by the trigger spring 80 into engagement with the locking arms 152, which then couple the release gear 110 to the chassis 150. The release gear 110 is therefore fixed rotationally during dose set. This in turn prevents rotation of the belt gear 130 and, therefore, release of the belt 121.

Figure 19A:
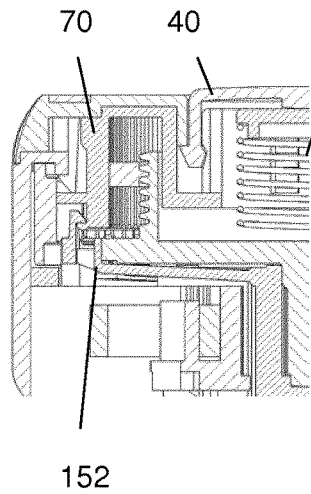
FIGS. 19a to 19c show a trigger actuation sequence of the device of FIG. 1, FIGS. 20a, 20b show details of the device of FIG. 1, FIGS. 21a to 21c show an end of dose click sequence of the device of FIG. 1, FIGS. 22a to 22c sectional views of a detail of a drug delivery device according to a second embodiment.
Figure 19B:
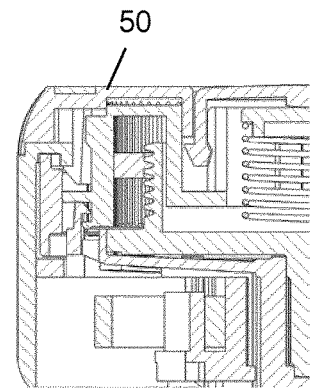
Figure 19C:
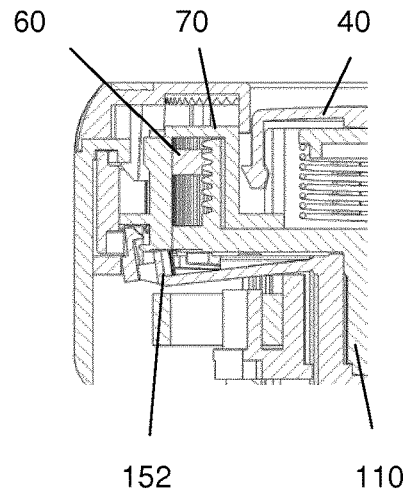

The device may be triggered by the user through application of an axial force on the trigger 40 (FIG. 19a). The trigger 40 acts on the dial gear 70, translating the dial gear 70 and chassis locking arms 152, compressing the trigger spring 80. As the dial gear 70 translates it first decouples from the dial member 50 as the face teeth disengage. At this stage (mid trigger position, FIG. 19b) the dial member 50 can no longer be rotated in either direction since the dial member 50 detent arm 53 is prevented from deflecting by an annular abutment on the dial gear 70. Further translation of the trigger 40 couples the dial gear 70 to release gear 110 via splines and finally decouples the release gear 110 from the chassis 150 (FIG. 19c).

On triggering, the release gear 110 rotates, controlled by the dial gear 70 and number wheel 100. The belt gear 130 rotates, due to the torque generated by the main spring 140 acting through the belt 121. As the main spring 140 extends, the plunger 122 is driven against the bung, creating a distal translation and causing medicament to be dispensed. Since the release gear 110, dial gear 70 and number wheel 100 are rotationally coupled, the number wheel 100 also rotates during dispense in a counter-clockwise direction, returning towards the zero unit stop 101, 153. At the zero unit position the number wheel 100 contacts the abutment 153 on the chassis 150, preventing further rotation of the dial gear 70, release gear 110 and belt gear 130, stopping release of the belt 121 and any further dispense of medicament.

The trigger 40 is subsequently released, re-engaging the chassis locking arms 152 to lock the rotational position of the release gear 110, belt gear 130, belt 121, plunger 122 and main spring 140 independently from the zero unit stop between chassis 150 and number wheel 100. This allows the next dose to be set without immediate release of the main spring 140. Aside from the last dose nut 60, release gear 110, belt gear 130, belt 121, plunger 122 and main spring 140 all other components in the device return to their original positions once the entire dose has completed dispense.

Figure 20A:
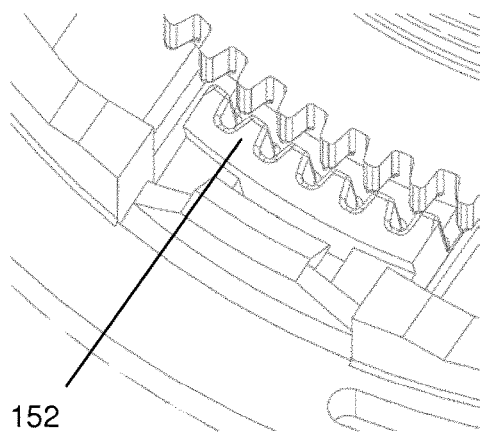
Figure 20B:
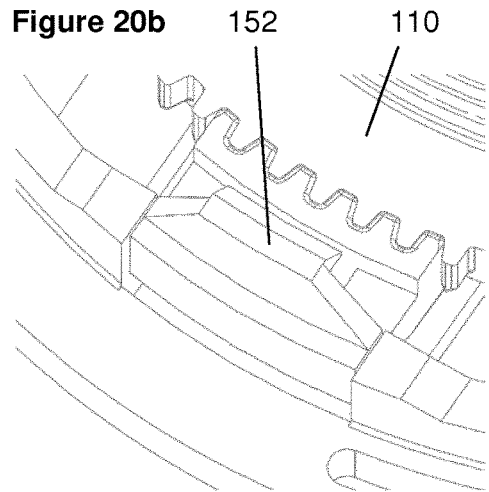

The release gear 110 splines that engage with the chassis locking arms 152 are angled so the release gear 110 is turned against the torque induced by the main spring 140 as they re-engage when the trigger 40 is released (FIGS. 20a, 20b). Back-winding the release gear 110 ensures that the chassis locking arms 152 react the main spring 140 force in place of the zero unit stop as the trigger 40 is released. This prevents the release gear 110 rotating to take up clearance at this interface when the subsequent dose is dialed (and the zero unit stop is disengaged), which could lead to the dispense of some fluid.

Feedback is provided to the user during dose setting by the interaction between the dial member 50 detent arm 53 and the body 10 ratchet features 11. Dispense feedback is created through interaction between the chassis 150 and ratchet features on the release gear 110. A cantilever arm on the chassis 150 rides over the ratchet features on the release gear 110.

Figure 21A:
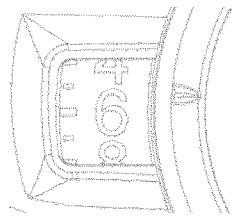
Figure 21B:
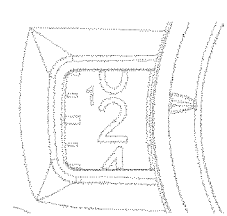
Figure 21C:
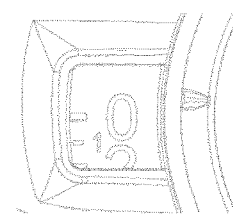
Figure 21C:
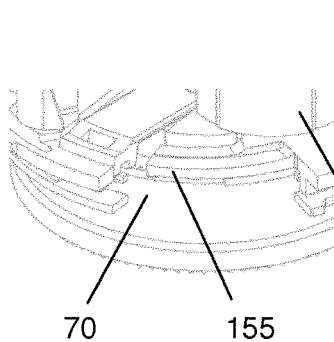
Figure 21C:
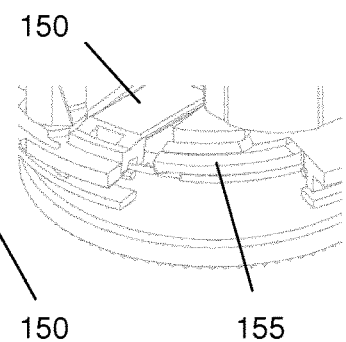
Figure 21C:
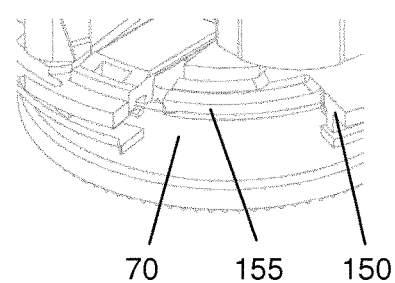

A single, distinctive click is created as the device returns to the zero unit stop. This provides clear feedback to the user that the dose has been completed in addition to the dispense clicker ceasing. A cantilever arm 155 in the chassis 150 engages with the dial gear 70 when in the dispense condition. This arm is deflected as the dial gear 70 approaches the zero unit stop and rapidly released as the dial gear 70 engages the zero unit stop (FIGS. 21a to 21c).

It is possible to incorporate a mechanism that allows the user to control the speed of dispense by the distance that they move the trigger 40. In this second embodiment the features and functions are identical to the first embodiment as described above. However, an additional system 160 is included as shown in FIGS. 22a to 22c.

The embodiment shows a multiplate clutch system 160 integrated into the device acting between the dial member 50 (which is locked during dispense) and dial gear 70. The system comprises a carrier 161 which is splined to the dial member 50, a clutch spring 162 and a clutch pack comprising rotating plates 163 which are splined to the dial gear 70 and static plates 164 which are splined to the dial member 50 via carrier 161.

Figure 22A:
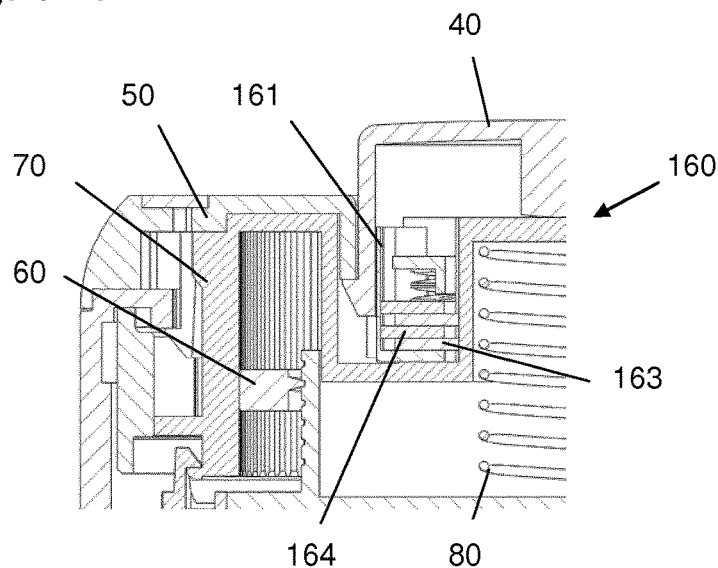
Figure 22B:
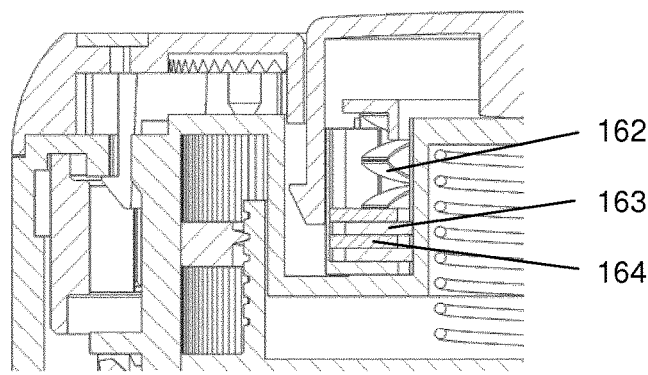
Figure 22C:
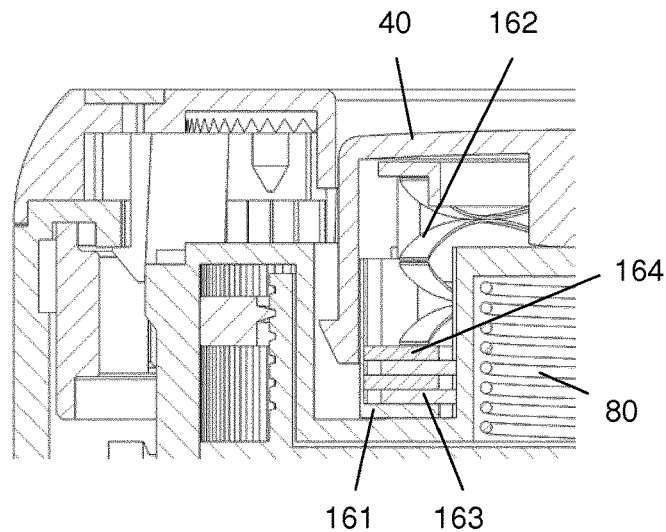

For the embodiment shown in FIGS. 22a to 22c, force applied to the clutch pack 163, 164 from the clutch spring 162 reduces as the trigger 40 is depressed. Multiple clutch plates 163, 164 increase the torque capacity of the clutch for a given clutch spring force. In this embodiment, the overall trigger 40 travel is increased by addition of the user variable speed control.

The facility for removing the need for a user to prime the device when first used can also be incorporated. This involves removing the variable distance (dependent on component and cartridge tolerances) between the cartridge bung 31 and the plunger 122 during manufacture such that the plunger 122 is in contact (and applies a small force) to the bung when assembled. This "prime elimination" is achieved using the following method: The cartridge holder 20 is divided into two separate components (cartridge holder 20 and rear body) and the device assembled omitting the rear body.

A small dose of approximately 10 units is dialed by rotating the dial member 50 as the user would. The belt gear 130 is rotationally coupled to an assembly tool with torque measurement capability. The trigger 40 is depressed to release the mechanism and the torque generated in the belt gear 130 is measured as it is rotated clockwise via the assembly tool, thus releasing belt 121. As the belt 121 is released, the plunger 122 approaches the bung 31 under the main spring 140 force. When the plunger 122 contacts the bung, the bung 31 will begin to react a proportion of the main spring 140 force, thus reducing the belt gear 130 torque. Measurement of this change in torque as the belt 121 is released allows a specific force to be applied to the bung by the main spring 140. Release of the trigger 40 subsequently locks the mechanism and any set doses remaining are then dialed to zero. Finally the rear body is clipped into position to complete the assembly.

Figure 23:
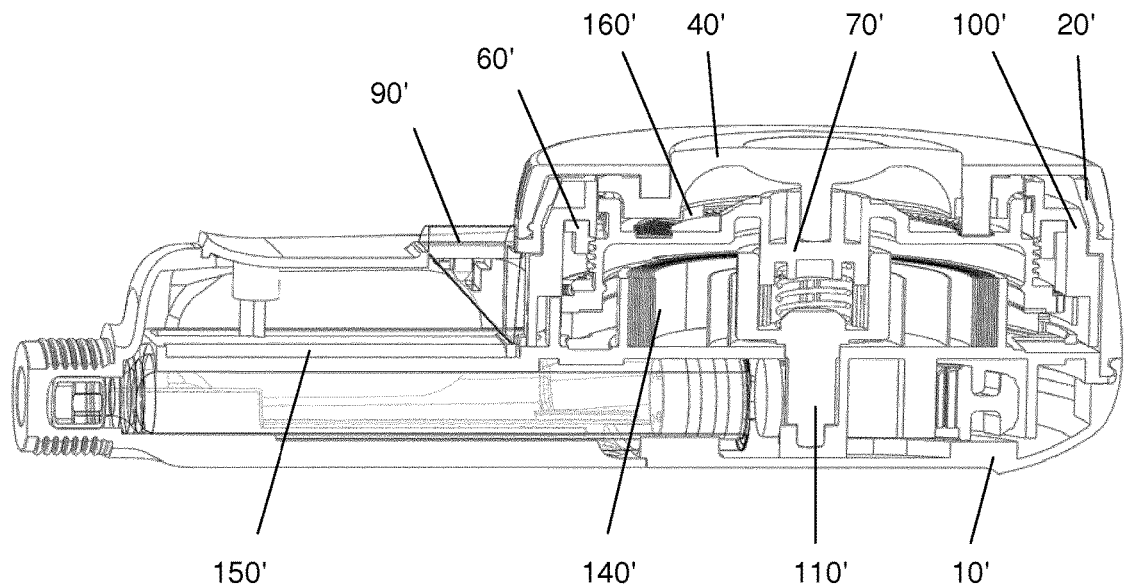
FIG. 23 shows a partially cut-open side view of an injection device according to a further embodiment of the disclosure.
Figure 24:
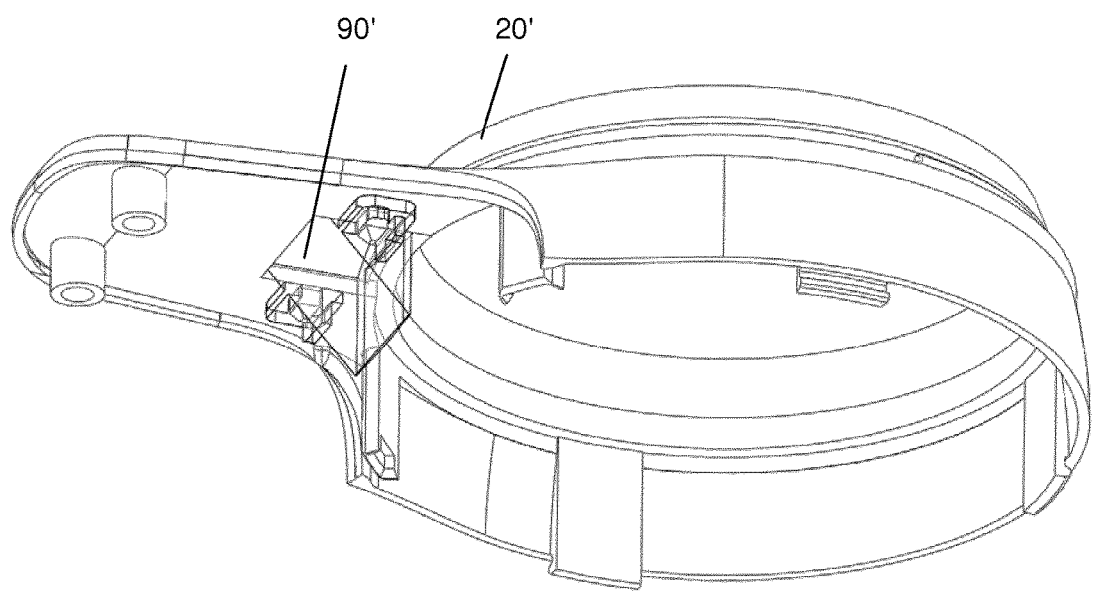
FIG. 24 shows a perspective view of the cartridge holder with attached prism of the embodiment of FIG. 23.

FIGS. 23 and 24 show a further embodiment of the present disclosure having a different drive mechanism compared with the embodiments of FIGS. 1 to 22c. As can be seen in FIG. 23, the injection device has a different geometry of the casework defined by body 10' and cartridge holder 20' with chassis 150' being elongated to extend towards the needle end of the cartridge within cartridge holder 20'. The last dose nut 60' is splined to a component part 100' having functions of the number wheel and the dial gear of the further embodiments included in one single part. Further, last dose nut 60' is threaded to the coupling gear 70'. The compression spring of the further embodiments is replaced by a power spring 140' in the form of a coiled band located between chassis 150' and release gear 110', which is separated from the pinion. A different dial ratchet 160' is arranged between trigger 40' and coupling gear 70'. In addition, the geometry of prism 90' is refined enhancing visibility and clarity of the dialed dose whilst reducing parallax errors of the display. The design of prism 90' is shown in FIG. 24 in more detail with the prism 90' being assembled to the cartridge holder 20'.

Comment: This embodiment comprises a totally different drive mechanism which requires a more detailed description. In contrast to the remark on slide 193 of HM65pre167_iss2.ppt, the layout of the last dose nut seems to be identical to e.g. FIG. 16, 19 or 22. Presently, I do not see major differences in the designs of the prisms. Please explain the amendments with respect to FIGS. 1 to 22 and advantages resulting from these amendments in more detail.

The invention claimed is:

1. A drug delivery device comprising:
 a dose setting member for setting variable doses of a medicament; and
 a display for indicating a dose set by the dose setting member,
 wherein the display comprises a number wheel rotationally coupled to the dose setting member and rotatable about an axis, the number wheel comprising an outer circumference comprising a series of markings; and
 at least one prism configured to deviate an image of the series of markings of the number wheel,
 wherein the series of markings of the number wheel are visible on the display when viewed through the at least one prism, and wherein the at least one prism is arranged such that the image of the series of markings of the number wheel is deviated to be viewed in a direction parallel to the axis of the number wheel.

2. The drug delivery device according to claim 1, wherein the at least one prism is a triangular prism, and the series of markings is provided mirrored on the outer circumference of the number wheel.

3. The drug delivery device according to claim 1, wherein the at least one prism comprises a penta-prism, and the series of markings is provided non-mirrored on the outer circumference of the number wheel.

4. The drug delivery device according to claim 1, wherein the at least one prism magnifies the series of markings on the number wheel.

5. The drug delivery device according to claim 1, comprising a housing having a longitudinal axis defined by a compartment, the compartment configured to receive a cartridge, wherein the dose setting member is configured to rotate within the housing about an axis of rotation, wherein the axis of rotation is perpendicular to the longitudinal axis of the housing.

6. The drug delivery device according to claim 1, comprising a drive mechanism, the drive mechanism comprising:
 a plunger configured to act on a bung of a cartridge;
 a pressure spring configured to act on the plunger;
 a retaining member coupled to the plunger; and
 a release member operable between a first state and a second state, wherein in the first state the release member is rotationally constrained, and in the second state the release member is rotatable, thus allowing movement of the plunger.

7. The drug delivery device of claim 6, wherein the retaining member is a flexible belt or cable.

8. The drug delivery device of claim 6, wherein the retaining member is attached to and wound on a drum which is in gear engagement with the release member.

9. The drug delivery device according to claim 6, wherein the dose setting member is configured to rotate relative to the release member during the dose setting and is configured to rotate together with the release member during a dose dispensing.

10. The drug delivery device according to claim 6, wherein rotation of the dose setting member is limited by a plurality of rotational stops defining a minimum dose position and a maximum dose position.

11. The drug delivery device according to claim 6, comprising a trigger being axially movable in the direction of an axis of rotation of the dose setting member, wherein actuation of the trigger switches the release member between the first state and the second state.

12. The drug delivery device according to claim 6, comprising:
 a dose dial grip; and
 a clutch, wherein the clutch rotationally couples the dose dial grip to the dose setting member during the dose setting, and the clutch rotationally de-couples the dose dial grip from the dose setting member and rotationally couples the dose setting member to the release member during a dose dispensing.

13. The drug delivery device according to claim 6, comprising a nut, wherein the nut is guided axially displaceable and non-rotatable with respect to one of the dose setting member and the release member, and the nut is in threaded engagement with the other of the dose setting member and the release member such that relative rotation between the dose setting member and the release member during the dose setting causes the nut to move towards an end stop.

14. The drug delivery device according to claim 13, wherein the nut prevents setting of a dose exceeding an amount of the medicament in the cartridge.

15. The drug delivery device according to claim 1, comprising a cartridge containing the medicament.

16. The drug delivery device according to claim 15, wherein the medicament comprises a pharmaceutically active compound.

17. The drug delivery device according to claim 1, wherein the at least one prism deviates the image of the series of markings of the number wheel by 90°.

* * * * *